United States Patent
Labute

(10) Patent No.: US 6,691,045 B1
(45) Date of Patent: *Feb. 10, 2004

(54) METHOD FOR DETERMINING DISCRETE QUANTITATIVE STRUCTURE ACTIVITY RELATIONSHIPS

(75) Inventor: Paul R. Labute, Outremont (CA)

(73) Assignee: Chemical Computing Group Inc., Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,912

(22) Filed: Feb. 19, 1999

(30) Foreign Application Priority Data

Feb. 19, 1998 (GB) .............................................. 9803466

(51) Int. Cl.⁷ ........................ G01N 33/48; G01N 31/00; G01N 35/00; G06F 19/00
(52) U.S. Cl. ............................... 702/27; 436/8; 436/43; 702/19
(58) Field of Search .................. 364/496, 497, 364/499, 578; 436/8, 43; 702/19, 27

(56) References Cited

U.S. PATENT DOCUMENTS

| | | | |
|---|---|---|---|
| 5,025,388 A | 6/1991 | Cramer, III et al. | 364/496 |
| 5,434,796 A | 7/1995 | Weininger | 364/496 |
| 5,463,564 A | 10/1995 | Agrafiotis et al. | 364/496 |
| 5,526,281 A | 6/1996 | Chapman et al. | 364/496 |
| 5,574,656 A | 11/1996 | Agrafiotis et al. | 364/500 |
| 5,684,711 A | 11/1997 | Agrafiotis et al. | 364/500 |
| 5,699,268 A | 12/1997 | Schmidt | 364/496 |
| 5,703,792 A | 12/1997 | Chapman | 364/496 |

OTHER PUBLICATIONS

Hua Gao et al., Binary Quantitative Structure–Activity Relationship (QSAR) Analysis of Estrogen Receptor Ligands, *Journal of Chemical Information and Computer Sciences*, 1999, vol. 39, No. 1, pp. 164–168.

P. Labute, Binary QSAR: A method for the Determination of Quantitative Structure Activity Relationships, *Pacific Symposium on Biocomputing '99*, Jan. 4–9, 1999, pp. 444–455.

"Prediction of Polymer Properties", Second Edition, Revised and Expanded, by Jozef Bicerano, © 1996 by Marcel Dekker, Inc., New York, 14 pp.: cover page, Library of Congress Cataloging–in–Publication Data page, 17–25, 55, 67, and 96.

*Primary Examiner*—Ardin H. Marschel
(74) *Attorney, Agent, or Firm*—Shlesinger, Arkwright & Garvey LLP

(57) ABSTRACT

Method for developing a quantitative structure activity relationship that includes obtaining a training set of chemical compounds with molecular descriptors consisting of a number of multidimensional vectors with an activity class for each of the vectors; partitioning the multidimensional vectors into groups having interdependence; transforming the descriptors such that the interdependence of the groups is lessened; estimating a probability distribution of the descriptors by assuming that a probability distribution of a product of each of the groups is approximately equal to the probability distribution of the molecular descriptors; performing the partitioning, transforming and estimating steps for each of the activity classes; and, developing a probability distribution for the activity classes.

40 Claims, 6 Drawing Sheets

METHOD FOR DETERMINING DISCRETE QUANTITATIVE STRUCTURE ACTIVITY RELATIONSHIPS

FIELD OF THE INVENTION

This invention relates generally to the method of determining relationships between the structure or properties of chemical compounds and the biological activity of those compounds.

BACKGROUND OF THE INVENTION

The pharmaceutical and biotechnology industries are continuously searching for effective therapeutic or diagnostic agents. The processes for finding effective agents includes target identification, ligand identification, toxicology and clinical trials.

Target identification is basically the identification of a particular biological component, namely a protein and its association with particular disease states or regulatory systems. A protein identified in a search for a chemical compound (drug) that can affect a disease or its symptoms is called a target. Protein are large chemical compound comprising a polymer chain of amino acids. The word protein is used herein to refer to any chemical compound that is involved in the regulation or control of biological systems (e.g. enzymes) and whose function can be interfered with by a drug.

The word disease is used herein to refer to an acquired condition or genetic condition. A disease can alter the normal biological systems of the body, causing an over or under abundance of chemical compounds (i.e. a "chemical imbalance"). The regulatory systems for these chemical compounds involve the use, by the body, of certain proteins to detect imbalances or cause the body to produce neutralizing compounds in an attempt to restore the chemical imbalance. The word body is used herein to refer to any biological system: e.g. plant, animal or bacterial.

Ligand identification includes search for a chemical compound that binds to a particular target. A ligand is a chemical compound that can attach itself to a protein and interfere with the normal functioning of the protein. A useful analogy is viewing the protein as a "lock" and the ligand as a "key." A ligand that fits the "lock" is called "active."

Toxicology and clinical trials involve characterizing the effects on the entire body of an identified ligand for a particular target. Additionally, the overall effectiveness regarding the disease must also be measured. These efforts are conducted in model bodies (i.e. generally animals) and then ultimately on the intended body (i.e. generally humans).

The present invention relates to ligand identification. In other words, a target has been identified and the identity of an active ligand is desired. Ligand identification generally involves the developing of a hypothesis that a particular chemical compound will be active, performing a physical experiment to determine if the hypothesized compound is active, and if the compound is not active, then returning to the step of developing a hypothesis.

There are several methods available for developing hypotheses that a particular chemical compound will be active.

A very slow and unpredictable process is introspection. That is, the expertise gained by humans in the hypothesis-experiment process can be put to use in developing new hypotheses regarding the selection of candidate ligands.

Computer simulation methods have also been proposed to reduce the cost of physical experiments. These methods include simulations of activity and suggestions for new candidate ligands. These simulations have not had broad success and are generally too slow and unreliable unless a number of active compounds have already been discovered and minor modifications are desired to improve some property.

The current method of choice is generally called high throughput screening (HTS). This includes the automation of the physical experiment step with robots so that hundreds of thousands or millions of experiments can be performed in a short period of time. This process has allowed a brute-force approach to ligand discovery. The hypothesis phase consists of obtaining large collections of molecules either from external suppliers or through combinatorial chemistry type production of large numbers of compounds. Combinatorial chemistry is a methodology in which many chemical reactions are performed simultaneously to produce a large collection of compounds. The large collection of compounds can then be physically tested with robots and activity results measured.

The universe of possible ligands is extremely large; estimated between $10^{40}$ and $10^{400}$ compounds. Accordingly, even with HTS approaches it is impossible to physically test all possible ligand candidates. Thus, methods are needed to discard the majority of the possibilities in advance or as the search proceeds.

It is generally accepted that the structure, composition, or physical properties of a ligand directly affect its biological activity against a target. The attempt to transform this qualitative belief into a quantitative method of activity assessment is known as the determination of Quantitative Structure Activity Relationships, or QSAR. QSAR began with the work of Hansch and was further developed by others. See, Hansch, C., Fujita, T, ρ-σ-π Analysis, A Method for the Correlation of Biological Activity and Chemical Structure, J.Am.Chem.Soc. 1964; Cramer, R. D., Patterson, D. E., Gunce, J. D., Comparative Molecular Field Analysis (CoMFA), 1. Effect of Shape on Binding of Steroids to Carrier Proteins, J.Am.Chem.Soc., 1988, 110, 5959–5967; and, Roger, D., Hopfinger, A. J., Application of Genetic Function Approximation to Quantitative Structure-Activity Relationships and Quantitative Structure-Property Relationships, J.Chem.Info.Comp.Sci., 1994, 34.

Determining a QSAR generally includes the following steps:

First, a quantitative measure of activity needs to be defined.

Second, the ligand needs to be expressed in some quantitative manner. This step generally includes selecting a collection of numbers that characterize the ligand. These numbers are called molecular descriptors or descriptors.

Then, a functional relationship between activity and the selected descriptors must be determined. This includes developing a mathematical function that has the property that "activity=a function of the descriptors", to a suitable high level of accuracy.

The functional relationship and the molecular descriptors are generally used to predict the activity of new candidate ligands.

Activity is traditionally measured as the amount of ligand needed to produce a particular interference with a target. The amount needed is on a continuous scale.

The selection of molecular descriptors is usually target-specific. Physical properties are often used. Mathematical properties based on the line drawing of a chemical compounds are also used. The use of the electric field of the ligand as a molecular descriptor is called Comparative Molecular Field Analysis (CoMFA) and has been the subject of previous patents. Other molecular descriptor sets include "fingerprints" or holograms", which are descriptions of small sub-structures in the ligand.

The most widely used method of determining the functional relationship is the statistical technique of regression or least squares. Techniques such as genetic algorithms and partial least squares are used to select the "important" descriptors from the "less important" descriptors or "noise".

The use of high throughput screening (HTS) to identify active compounds has greatly challenged commonly used QSAR techniques. HTS usually generates large amounts of assay data, which initially classifies compounds as active or inactive. In addition, compounds in screening libraries are typically noncongeneric, i.e., they do not share similar core structures. This makes it difficult, if not impossible, to analyze HTS data by classical QSAR techniques and to predict active compounds.

Higher throughput reduces the precision of the activity measurement. Many HTS technologies report a binary condition; a candidate ligand is either "active" or "inactive". Some HTS technologies report a discrete measure; i.e. activity on a scale of 1 to 10. In either case, classical QSAR techniques require a continuous activity measurement, e.g. accurate to two to three decimal places.

Many HTS techniques have the unfortunate property that the activity measurement is error prone. The error rate is significant enough to warrant special attention since classical QSAR technology is very sensitive to error and outliers (data extremes). A significant error rate will neutralize the predictive capabilities of classical QSAR technology.

To exemplify, consider the following simple example. Suppose that activity y is linearly related to a single descriptor x. The linear relationship is expressed as follows:

$$y = mx + b$$

A conventional data set would consist of n observations $(y_i, x_i)$. Without loss of generality it may be assumed that the slope is greater than zero, m>0 the $x_i$ have mean 0 and variance 1, and that activity is indicated by the condition that $$y < 0 \left( i.e. \text{ when } x < \frac{-b}{m} \right).$$

Using linear regression, the estimates for m and b are:

$$\hat{m} = \frac{1}{n} \sum_{i=1}^{n} y_i x_i, \quad \hat{b} = \bar{y}, \quad \bar{y} = \frac{1}{n} \sum_{i=1}^{n} y_i$$

When presented with HTS binary measurements (i.e. 1 is active and 0 is inactive) representing the condition that $y_i<0$ the linear regression estimates become:

$$\hat{m} = \frac{1}{n} \sum_{xi<b/m} x_i \quad \hat{b} = \frac{a}{n}$$

where a is the number of active compounds. These estimates are completely different than those obtained from non-binary input (e.g., the b estimate is always in the range [0,1] for binary data). For example, the estimated descriptor value at the boundary between active and inactive is:

$$x = \frac{-1}{\sum_{xi<-b/m} x_i / a}$$

This is inversely proportional to the mean active descriptor value. Contrast the above equation, which was developed with linear regression, with −b/m, the true descriptor value at the boundary. The assumptions of linear regression are not satisfied with binary HTS data.

OBJECTS AND SUMMARY OF THE INVENTION

It is an object of the present invention to provide a method for developing a quantitative structure activity relationship that overcomes the shortfalls of the prior art.

Another object of the present invention is to provide a method for developing a quantitative structure activity relationship that allows the prediction of a candidate compound for a particular target to be identified as either active or inactive.

A further object of the present invention is to provide a method for developing a quantitative structure activity relationship that is less sensitive to High Throughput Screening input data error and outliers than the prior art.

Still a further object of the present invention is to provide a method for developing a quantitative structure activity relationship and analyze candidate compounds with the use of computer equipment.

Yet a further object of present invention is to provide a method for developing a quantitative structure activity relationship that is not significantly influenced by data boundary effects.

Still a further object of the present invention is to predict whether or not a chemical compound is a member of a particular set.

Yet another object of this present invention is to provide a method for developing a quantitative structure activity relationship that includes obtaining a training set of chemical compounds with molecular descriptors consisting of a number of multidimensional vectors with an activity class for each of the vectors; partitioning the multidimensional vectors in groups having interdependence; transforming the descriptors such that the interdependence of the groups is lessened; estimating a probability distribution of the descriptors by assuming that the probability distribution of the product of each of the groups is approximately equal to the probability distribution of the molecular descriptors; performing the partitioning, transforming and estimating steps for each of the activity classes; and, developing a probability distribution for the activity classes.

Still a further object of the present invention is to provide a method for predicting activity of candidate ligands that includes developing a prediction model; obtaining a candidate chemical compound; and, applying the prediction model to the candidate compound.

Yet another object of the present invention is to provide a system for predicting activity of candidate compounds as either active or inactive that includes an analyzer that receives a training set of chemical compounds; a prediction model developed by the analyzer and is based on the training set; and, a sorter that receives a candidate ligand and receives the model from the analyzer, the sorter applies the model to the candidate ligand to predict the activity of the candidate ligand.

Still a further object of the present invention is to provide a computer-based method of generating a quantitative structure activity relationship that includes calculating a numerical representation of molecules consisting of n numbers per molecule; and, estimating a probability distribution that a molecules is active.

DETAILED DESCRIPTION OF THE PREFERRED EMBODIMENTS

Figure 1:
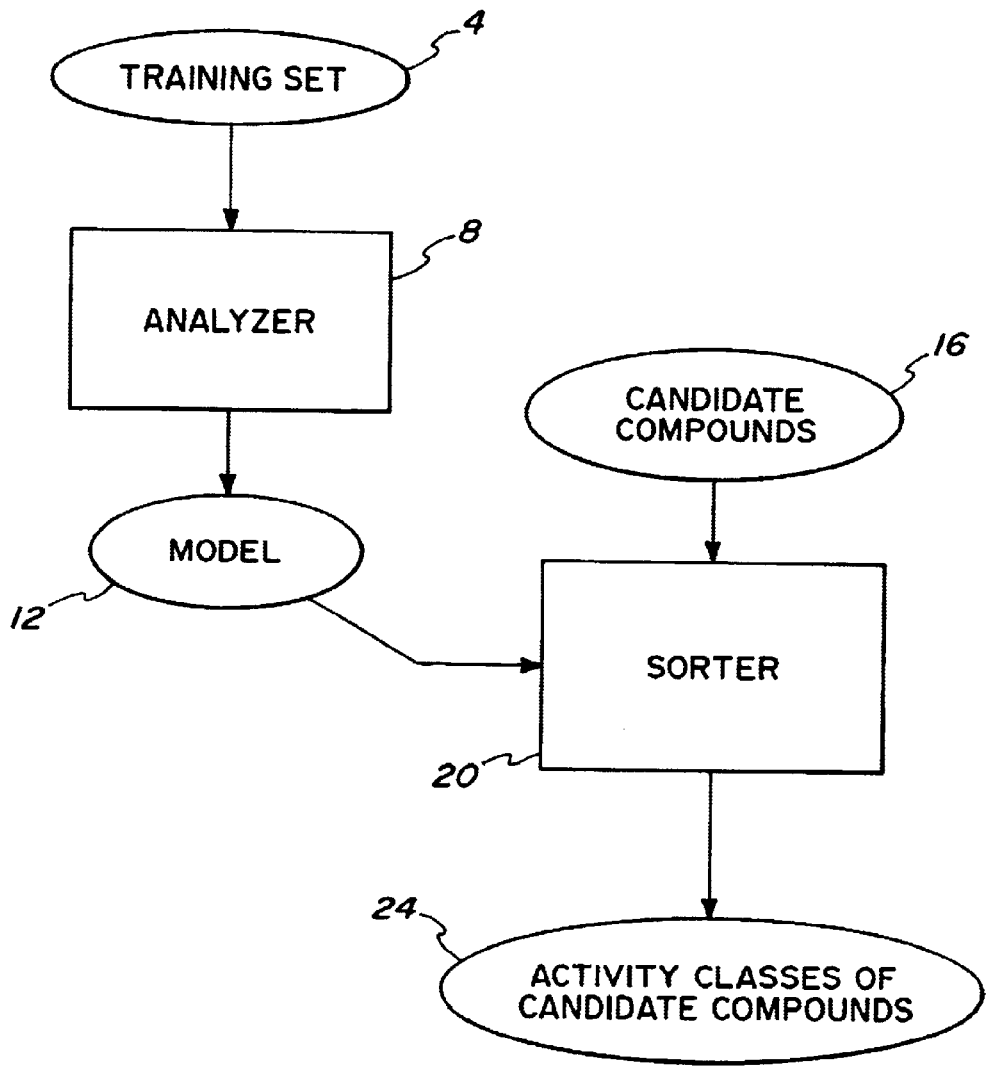
FIG. 1 is a flow diagram of the method of the present invention.

FIG. 1 is a flow chart of the present invention, showing the overall structure of the method of developing a discrete Quantitative Structure Activity Relationship (QSAR), and applying the discrete QSAR to candidate compounds to determine the probability that a particular candidate will be active.

A training set of compounds 4 is obtained. Training set 4 are results from High Throughput Screening (HTS) experiments. Training set 4 may be data from other sources other than HTS, even virtual or hypothetical data.

Training set 4 comprises molecular descriptors to describe the chemical structures of the compounds, and the activity classes or discrete binding affinities associated with the descriptors.

Training set 4 is sent to an analyzer 8 to develop a model 12. Analyzer 8 is a computer. The functions of analyzer 8 may alternatively be performed by some other means, even by hand calculations. Analyzer 8 will be described further below.

Model 12 is a mathematical function that is the output of Analyzer 8. Model 12 is developed based on the 4 chemical structures of the training set 4 and the activity classes associated therewith, as will be thoroughly discussed below.

Candidate compounds 16 and model 12 are sent to a sorter 20. Candidate compounds 16 are experimental data. However, candidate compounds 16 may be from any source, even virtual or hypothetical compounds.

Sorter 20 applies model 12 to candidate compounds 16 to determine the activity of each candidate compound 16 for a particular target. Sorter 20 is a computer. The functions of sorter 20 may be performed by other means, such as hand calculations. Sorter 20 will be described further below.

Analyzer 8 and sorter 20 are connected together, to allow sorter 20 to receive model 12, and to a display device, not shown. The display device will allow a user to inspect the outputs of analyzer 8 and sorter 20. The display device is preferably a computer monitor. However, the display device may also be a printer, etc.

An example of a type of computer software program that will perform the methods described herein is entitled "Molecular Operating Environment" available through a license from the Chemical Computing Group Inc. of Montreal, Quebec, Canada.

Figure 2:
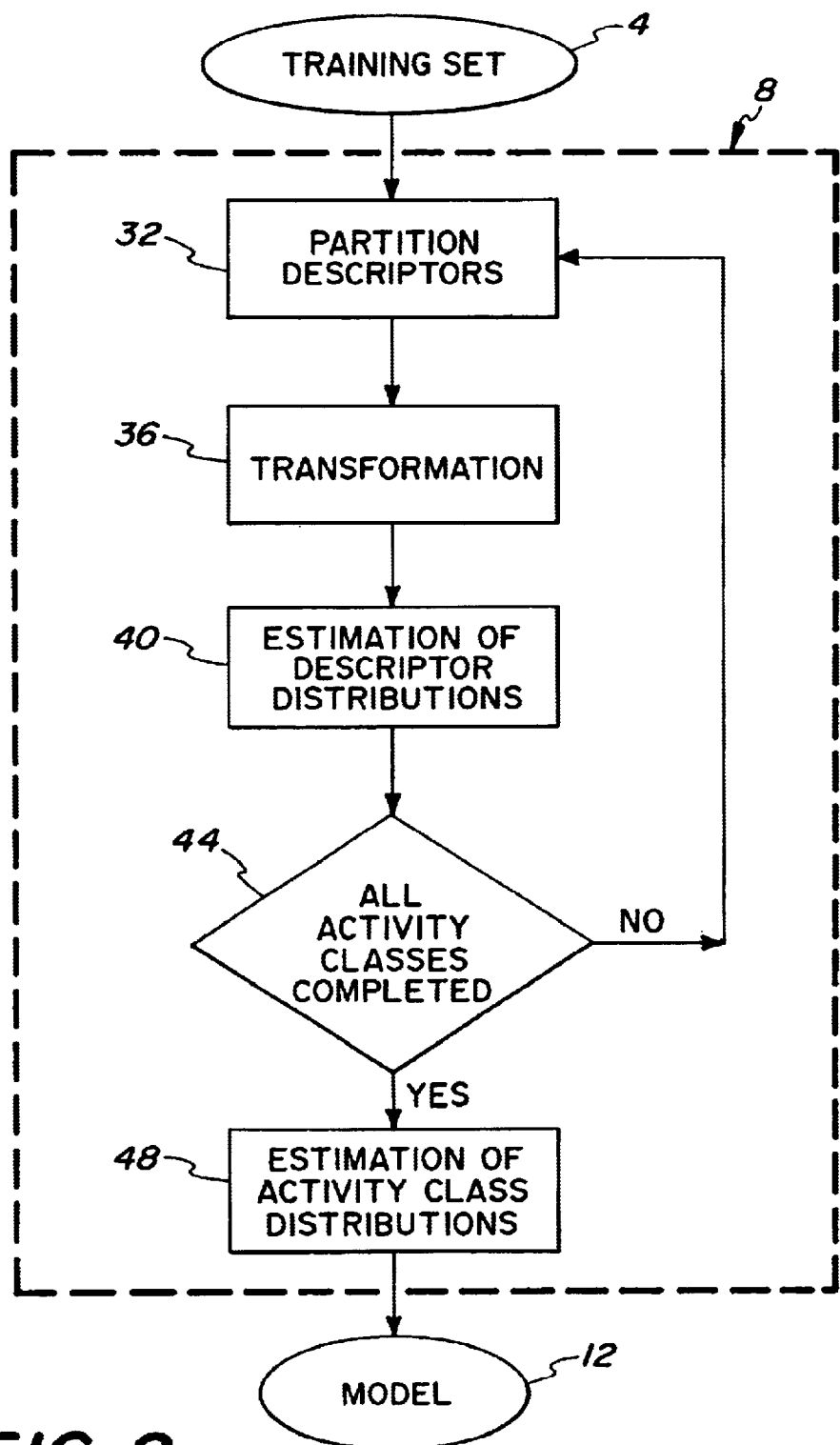
FIG. 2 is a flow diagram of the analyzer with its input and output.

FIG. 2 displays the overall general process that analyzer 8 performs, along with its input, training set 4, and its output, model 12. The following is a description of the steps shown in FIG. 2; more mathematical detail is set forth below.

Training set 4 is characterized by a number of multidimensional molecular descriptor vectors with an activity class associated with every vector.

The multidimensional descriptor vectors of training set 4 are partitioned into groups, 32. This partition is arbitrary. The only restriction is the fact that the higher the dimension, the more data is needed and more computer memory is needed. The groups have interdependence.

As represented by 36, the molecular descriptors are transformed to lessen the interdependence of the groups. Transformation will be discussed further below.

To estimate the distribution of the original molecular descriptors, the product of the distributions of each of the groups is assumed to approximately equal the distribution of the original molecular descriptors, as represented by 40.

Steps 32, 36 and 40 need to be performed for each activity class, as represented by 44.

The distribution of the activity classes must also be estimated 48.

With all of the distributions estimated, they are combined to establish a prediction function, i.e. model 12, that will determine whether a candidate compound belongs to a particular activity class.

Figure 3:
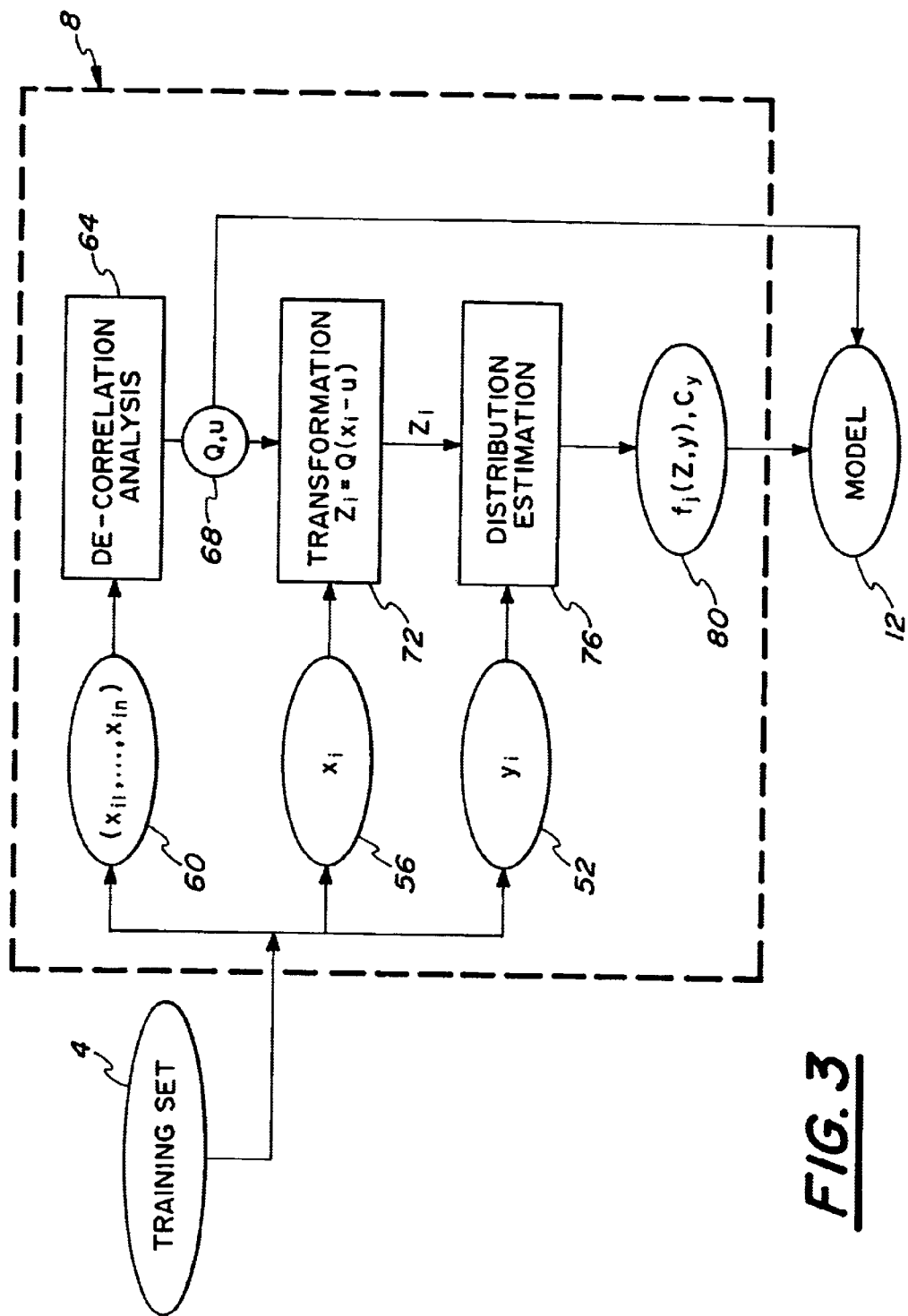
FIG. 3 is a mathematical flow diagram of the analyzer with its input and output.

The mathematical methods employed in the above steps will now be set forth for the particular case of a partition into groups of size 1 and a single transformation applicable to all classes. FIG. 3 displays the mathematical flow diagram for analyzer 8 and FIG. 4 displays the mathematical flow diagram for sorter 20.

Analyzer 8 accepts training set 4 data, which may be characterized by $\{(y_i, x_i)\}$. $y_i$ is represented by 52 and $x_i$ is represented by 56. Training set 4 is the results of m HTS experiments on a common target. Thus, there are m $(y_i, x_i)$'s where the $y_i$ are discrete values that without loss of generality, it may be assumed they are numbers $\{1, 2, \ldots, k\}$ and each $x_i$ is a vector each with n numbers (the molecular descriptors) and we write $x_i = (x_{i1}, \ldots, x_{in})$ represented by 60.

We will now introduce a random variable Y over the values $\{1, 2, \ldots k\}$, not shown in flow diagram, and a random variable over n-vectors (a random molecular descriptor), $X = (X_1 \ldots X_n)$, not shown in flow diagram.

The conditional distribution $Pr(Y|X)$ is used to determine the probability that a new molecule L, not shown, belongs to activity class y with $Pr(Y=y|X=L)$. The molecule can then be sorted into the class that has the highest probability, mathematically represented using the Bayes theorem:

$$Pr(Y = y \mid X = x) = \frac{Pr(X = x \mid Y = y)Pr(Y = y)}{\sum_{i=1}^{k} Pr(X = x \mid Y = i)Pr(Y = i)}$$

To use this formula for practical purposes it is necessary to analyze the HTS data in an effort to approximate the distributions on the right hand side of the equation.

The prior distribution of Y is estimated using a maximum likelihood estimator or a Bayes estimator. Any method of estimating these probabilities may be used. A Bayes estimator has been chosen, since it is well defined for all inputs, where Cj is the number of times that $y_i=j$ in the HTS experimental data:

$$Pr(Y=j) \approx g(j) = \frac{C_j + 1}{m + k}$$

Estimating the k distributions of the form $Pr(X=x|Y=j)$ is more problematic since the X is a vector of numbers: for values of n of five or more, a straightforward histogram build-up, or counting procedure cannot be used in practice because there will not be enough experimental data to approximate the distribution with any reasonable accuracy.

Our method to approximate the distributions of X is to transform a multidimensional distribution into a product f one dimensional distributions. However, it is understood herein, that rather than transforming into one dimensional distributions, the multidimensional distribution may be transformed into simply a collection of lesser dimensional distributions. The idea is to partition the multidimensional distributions into smaller groups to reduce the dimensions to enable one, or a computer, to work with the data.

Thus, to decorrelate 64 each multidimensional vector $x_i$, the method of principal component analysis is used to determine a,p by n linear transform Q and a n-vector u, collectively 68, such that the random variable $Z=Q(X-u)$ has a covariance matrix equal to the p by p identity matrix. For the purposes of approximation, it is assumed that the individual coordinates of Z are independent so that the following approximation can be made and is represented as 68 in FIG. 3:

$$Pr(X=x|Y=y) \approx Pr(Z=Q(x-u)|Y=y) = \prod_{i=1}^{p} Pr(Z_i=z_i|Y=y)$$

A number of one dimensional distributions that have mean 0 and variance 1, over the reals must be estimated from the HTS experimental data, identified as 76 in FIG. 3. To perform this task, let W be a random variable over the reals and let f (w) be the probability density for W. The function, f, can be estimated by accumulating a histogram of the observed sample values on a set of B bins (b0,b1], ..., (bB–1bB] defined by B+1 numbers b,<bk+1, $b_0$ is minus infinity and $b_B$ is plus infinity. Any method of estimating continuous distributions, other than the one explained here, may be employed.

The usual procedure for counting the number of observations among m samples in bin k>0 is:

$$B_k = \sum_{i=1}^{m} \delta(w_i \in (b_{k-1}, b_k]) = \sum_{i=1}^{m} \int_{b_{k-1}}^{b_k} \delta(x - w_i) dx$$

This procedure has an unfortunate sensitivity to the selection of bin boundaries since observations close to a bin boundary are treated as if they were in the middle of one of the bins. In view of this sensitivity, it is desirous to spread the observations out over the bins. In other words, rather than having a single observation point, the observation will be blurred over several bins. Here, the blurring area is created by a bell-curve. However, any type of spreading or blurring may be used.

Accordingly, to reduce the sensitivity to the bin boundaries, the delta function in the above equation is replaced with a Gaussian, with variance $s_2$. This can be thought as an observation error as well as a smoothing parameter. The equation now becomes:

$$B_k = \sum_{i=1}^{m} \int_{b_{k-1}}^{b_k} \frac{1}{s\sqrt{2}} \exp\left[-\frac{1}{2}\frac{(x-w_i)^2}{s\sqrt{2}}\right] dx =$$

$$\frac{1}{2} \sum_{i=1}^{m} \left[ erf\left(\frac{b_k - w_i}{s\sqrt{2}}\right) - erf\left(\frac{b_{k-1} - w_i}{s\sqrt{2}}\right) \right]$$

Using the above techniques an estimation 76, is made for pk distributions from the HTS experimental data. In other words, we approximate the one dimensional distributions with $f_j(z,y)$ for j in $\{1 \ldots, p\}$ and y in $\{1, \ldots, k\}$., $f_j(z,y)$, $C_y$ is represented by 80 in FIG. 3. The final approximation, or model 12, with z=Q (x–u), is:

$$Pr(Y=y|X=x) \approx \frac{(C_y + 1) \prod_{j=1}^{p} f_j(z_j, y)}{\sum_{i=1}^{k} (C_i + 1) \prod_{j=1}^{p} f_j(z_j, i)}$$

Now that model 12 is developed, predictions for a candidate ligand c can be made in two ways. Depending on whether the activity classes are an ordered scale, a user will choose the class that has the maximum probability or use the expected class value for the prediction.

Figure 4:
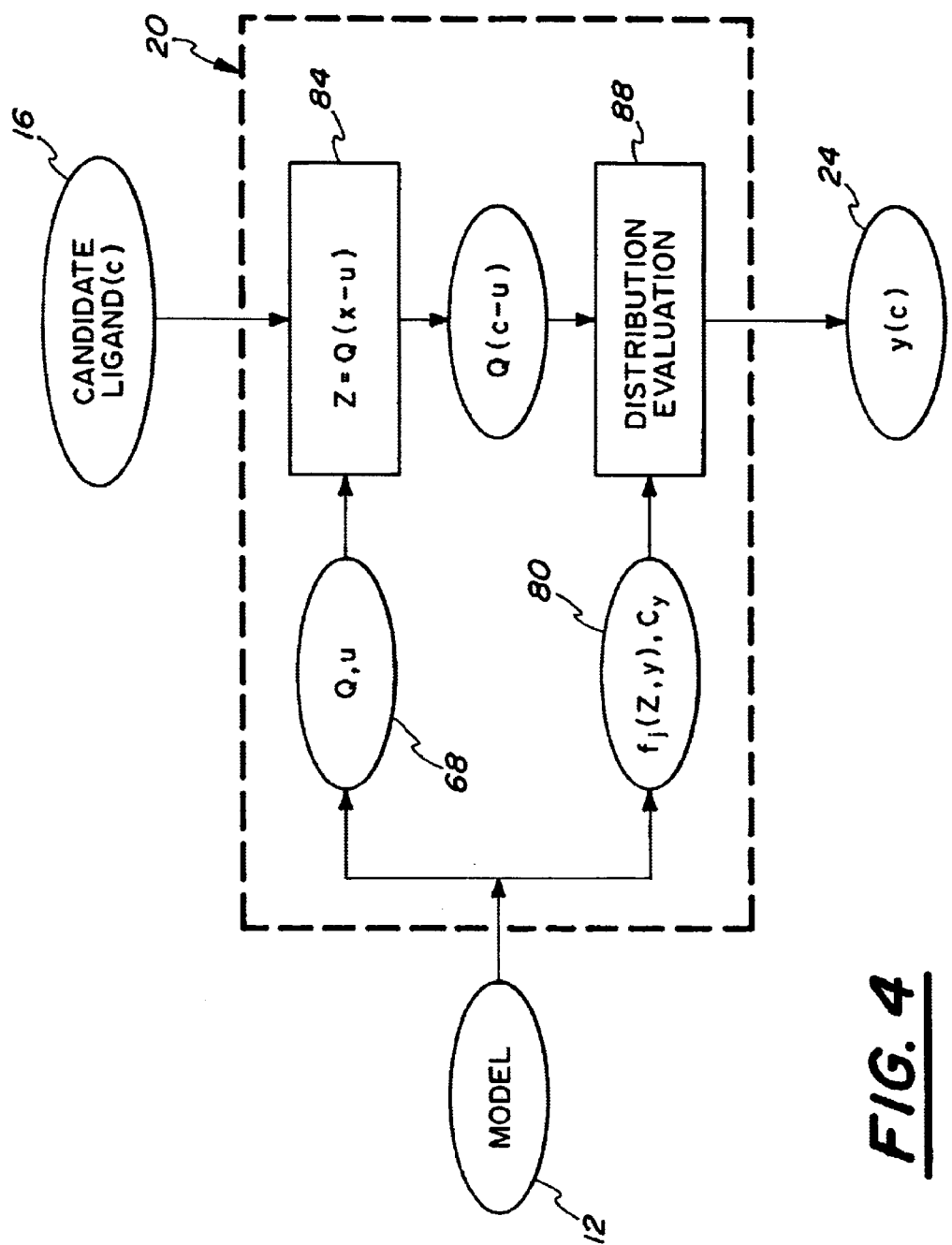
FIG. 4 is a mathematical flow diagram of the sorter with its input and output.

FIG. 4 displays the mathematical flow diagram for sorter 20. The input for sorter 20 is a candidate ligand c, 16, and model 12. The transform Q and n-vector u, 68, and $f_j(z,y)$, $C_y$, 80, make up model 12.

Candidate ligand 16 must go through the same process that each $x_i$ did as described above. These steps are represented as 84 and 88, which mimic 72 and 76 above. The output 24 of sorter 20 is the activity class of candidate ligand 16.

The steps outlined above are to be performed with the use of computer software and a computer. However, it is understood that the steps may be performed by some other means, even by manual calculations.

Use of the present invention typically will be iterative with efforts directed at selecting, determining, discovering or inventing those descriptors that lead to an accurate and predictive model of biological activity. A typical sequence of general QSAR steps, not necessarily the inventive steps, are the following.

Obtain a collection of chemical structures and a collection of activity classes numbers $\{y_1\}$ in the range $1, \ldots, k$ such that with each chemical structure, there is an associated activity class number.

For each chemical structure, calculate a set of descriptors $x=(x_1, \ldots, x_n)$. The complete input data set will be the $\{(y_i, x_i)\}$.

Apply the procedure described herein and depicted in is FIGS. 2 and 3 using the input data set training set as the set of "candidates" to obtain a "model" consisting of (Q, u, $f_j$, $C_y$) and a collection of model predictions $p_i$.

If the model predictions $\{p_i\}$ are in substantial agreement with the input activity classes $\{y_i\}$ and the model is judged to be suitably "predictive", then the model can be used to predict activity class of new candidates. Otherwise, the model can be adjusted by returning to the step of calculating a set of descriptors.

The model that is developed is then used to predict the activity class of a (possibly novel) chemical structure by calculating the same descriptors as were calculated in the step of calculating a set of descriptors for the model and by applying the model.

An objective of application of the present invention, as stated above, is to build a model to predict the 0 or 1 class when presented with chemical structure.

The present invention requires a numerical description of both the activity class and, for each activity class a vector of numbers (the descriptors, or quantification of the chemical structure). The source of the initial data set is quite arbitrary so long as a set of descriptors can be determined from the chemical structures. As mentioned above, the chemical structures need not refer to actual compounds; that is, they can be virtual compounds or hypothesized compounds. The activity classes can be any arbitrary classification of the structure; in most cases, this activity class will be some quantification or classification of biological activity.

Because the source of the data set is arbitrary, it is impossible to enumerate all possible ways in which a data set, or training set, can be assembled.

Research into scientific literature regarding experiments with the Carbonic Anhydrase II receptor revealed information describing physical experiments to determine and quantify the binding affinity of a variety of chemical compounds. Each compound is given a numerical value indicating its binding affinity. Table 1 depicts the nature of an example initial data set. Beside each drawing in Table 1, is a quantitative experimental assessment of binding affinity.

The activity data can be converted into, for example, two activity classes, "active" and "inactive", by comparison to a threshold value. For example purposes, the threshold value is picked at 5.85. If the activity value is less than 5.85, the activity class is 0. Otherwise, it would be 1. This results in the following data set depicted in Table 2.

It is preferred that the preparation of the initial data set would be performed by a computer. In such a case, the structures are drawn with commercially available chemical drawing programs or chemical information systems that return chemical structures. Such computer representations of chemical structures typically encode the connectivity and element labels of chemical structures. Some representations encode the depiction while some encode only the connectivity. For example, the same data of Table 2 can be represented textually using SMILES strings (a character-based encoding of chemical structures).

The nature of encoding of the chemical structures is not critical, as long as molecular descriptors can be calculated from the structure encoding.

A molecular descriptor is a number calculated from a chemical structure. For example, if chemical structures are encoded using chemical formulas, then the molecular weight of the structure is an example of a molecular descriptor. The molecular weight is a number that can be calculated from the chemical formula. It is preferred that the molecular descriptors be calculated by means of a computer. However, they may also be derived by mental calculations from introspection and examination of the data. Scientific literature contains many examples of descriptors used in QSAR studies. Examples of molecular descriptors are: molar refractivity; octinol/water partition coefficients; pKa; number carbons; number of triple bonds; number of aromatic atoms; sum of the positive partial charges on each atom; water accessible surface areas; heat of formation; topological connectivity indices; topological shape indices; electro topological state indices; structure fragment counts; van der Waals volume; etc. In general, the quality, accuracy and predictiveness of the calculated model will depend on which descriptors are chosen for a particular data set. Automatic and/or statistical methods are used to help select appropriate descriptors in the iterative model building procedure described herein.

As set forth above, the descriptors and activity classes are used to estimate the model parameters. The model can be used to "predict" or "back test" the activity classes of the training set. The statistical cross-validation procedures such, as "leave-one-out", may be used to estimate the quality and predictiveness of the model.

When the results of the model building and descriptor selection procedure are judged suitably accurate, the iterative procedure terminates. Exact termination criteria cannot be specified since accuracy and predictiveness will depend on the applications of the model. For example, a relative high accuracy of the model will be needed if the model is to be used to search databases of available compounds in an effort to locate compound with activity class "1". On the other hand, a less accurate model can be used if only a trend or gross indication of activity is required. In other words, the termination criteria are problem dependent.

To use the calculated model to predict activity classes of chemical structures not presented in the initial data training set, the following is performed. Each new structure is prepared in the same manner as the initial data set. The same molecular descriptors are calculated for the new structure and the vector of descriptors is used as input to the calculated model. The sorter, which utilizes the model, will output a predicted activity class. Typical uses of such a model would be compound data base searching, focusing on combinatorial libraries, or de novo design (the attempt to create new molecules by modification of chemical structures).

The following is based on and is a partial reproduction of: "Binary Quantitative Structure-Activity Relationship (QSAR) Analysis of Estrogen Receptor Ligands", Gao, H., Williams C., Labute P., Bajorath, J. *J.Chem.Inf.Comput.Sci* 1999, 39, 164–168, which is incorporated herein by reference.

The above methods for discrete or binary QSAR correlate compound structures, using molecular descriptors, with a "binary" expression of activity, i.e., 1=active and 0=inactive, and calculates a probability distribution for active and inactive compounds in a training set. This function can then be used to predict active compounds for a given target in a test set. The present invention is applied below to a drug discovery problem, the analysis of estrogen receptor ligands.

The estrogen receptor is an extensively studied pharmaceutical target for which a large number of ligand analogs have been generated and characterized. In addition, structural studies have elucidated the mechanism of the estrogen receptor-ligand interaction and identified the binding determinants. The estrogen receptor binding affinity data of estrogen analogs have been transformed into a binary data format. A predictive binary QSAR model has been derived and this model has been applied to a test set of other estrogen analogs. Both active and inactive analogs were predicted with high accuracy. The binary QSAR model was stable for a variety of binary activity cutoff values and the model was quite insensitive to boundary effects.

Figure 5:
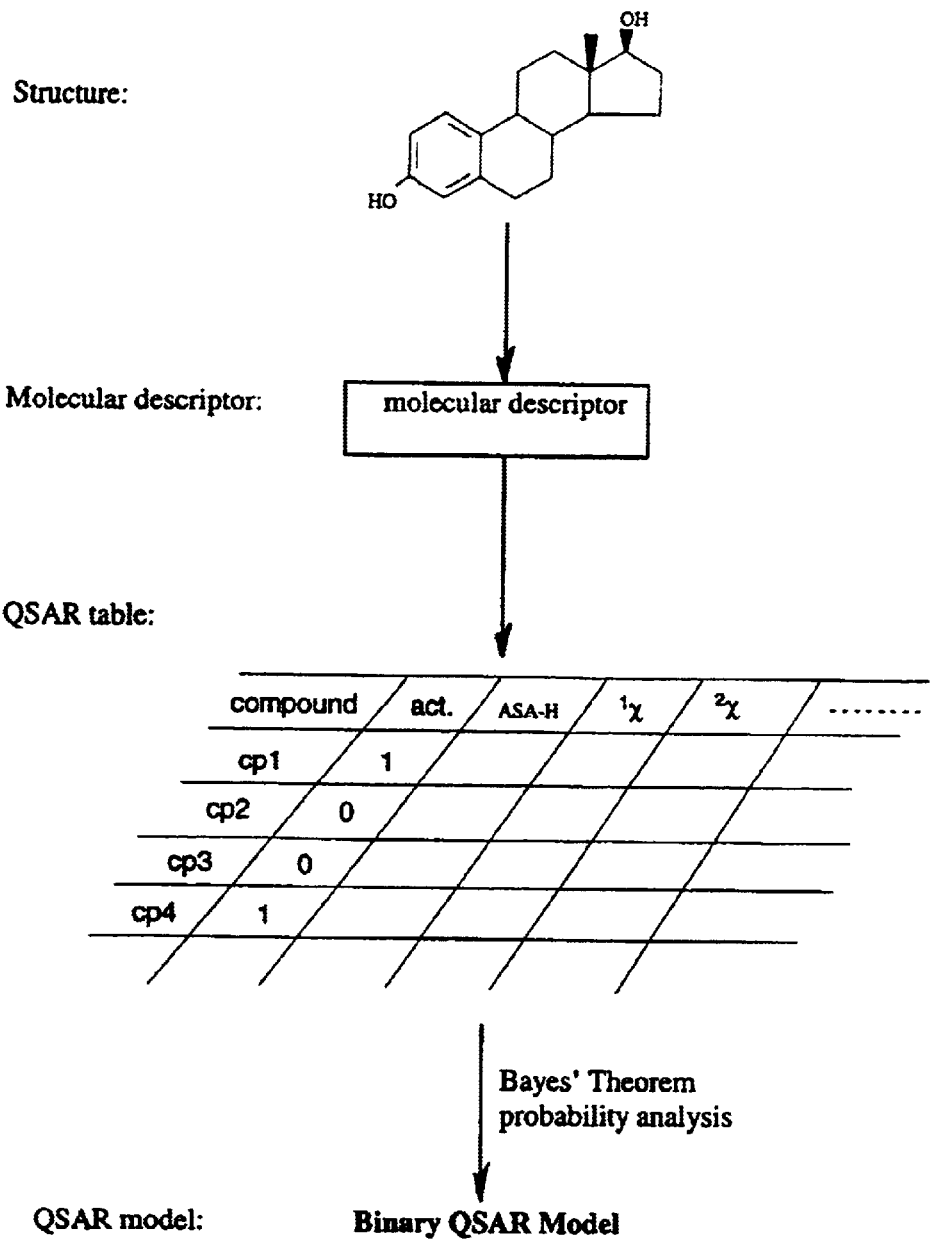
FIG. 5 is a flow diagram of binary QSAR analysis in MOE.

The binary QSAR analysis procedure used in this study are generally depicted in FIG. 5. Binary QSAR estimates, from a training set, the probability density $Pr(Y=1X=x)$ where Y is a Bernoulli random variable (i.e. Y takes on values of 0 or 1) representing "active" or "inactive" and X is a random n-vector or real numbers (a random collection of molecular descriptors).

A Principle Components Analysis (PCA) is conducted on the training set to calculate an n by p linear transform, $\underline{O}$, and an n-vector, u, such that the random p-vector $Z=\underline{O}(X-u)$ has mean and variance equal to the p by p identity matrix. The quantity p is referred to as the number of principle components.

The original molecular descriptors are transformed by $\underline{O}$ and u to obtain a decorrelated and normalized set of descriptors. The desired probability density is then approximated by applying Bayes' theorem and assuming that the transformed descriptors are mutually independent:

$$Pr(Y=1 \mid X=x) \approx \left[1 + \frac{pr(Y=0)}{Pr(Y=1)} \prod_{i=1}^{p} \frac{Pr(Z_i=z_i \mid Y=0)}{Pr(Z_i=z_i \mid y=1)}\right]^{-1}$$

Each probability density $Pr(Z_i=z_i)$ is estimated by constructing a histogram. Conventional procedures for histogram construction are sensitive to bin boundaries since every observation, no matter how close to a bin boundary, is treated as though it falls in the center of the bin. To reduce this sensitivity, each observation is replaced with a Gaussian density with variance $\sigma^2$. This variance can be interpreted as an observation error or as a smoothing parameter.

Once all of the 2p+2 probability densities have been estimated from the training set, the desired $Pr(Y=1/X=x)$ is constructed using the above formula.

The binding data of estrogen analogs to estrogen receptors of different species was collected from literature. There is little, if any, evidence for receptor-species difference in estrogen analog structure-affinity relationships. There are two subtypes of estrogen receptors, ER-$\alpha$ and ER-$\beta$. The data reported here is presumed to come from ER-$\alpha$, since this subtype is the predominant one in uterine and breast tissue. The binding data was placed on a common "relative binding affinity" (RBA) scale. Values on this scale were calculated as a percentage of the ratio or $IC_{50}$ values of test compounds to displace 50% of [$^3$H]estradiol from estrogen receptor binding. Thus, on the RBA scale, estradiol has a value of 100, with lower affinity analogs having lower values and higher affinity analogs higher RBA values. A total of 463 compounds were selected (tested for binding at 0 to 4° C.), 410 of which were used as a training set to derive a binary QSAR model, and 53 compounds as a test set to evaluate the model by predicting active and inactive compounds.

Table 4 shows the composition of estrogen analogs used in this analysis. The continuous biological activity data was expressed in binary form using a threshold criterion (log RBA). Any compounds with log RBA larger than or equal to this criterion were classified as active, and any compounds with lower log RBA values were classified as inactive. Different activity threshold values were used to alter the percentage of active compounds in the training set.

Molecular descriptors were calculated using 1998.03 version of MOE, from the Chemical Computing Group Inc. of Montreal, Quebec Canada, and binary QSAR analysis was carried out with the MOE binary QSAR function.

Performance of a binary QSAR model was measured as follows: let $m_0$ represent the number of active compounds, $m_1$ the number of inactive compounds, $c_0$ the number of active compounds correctly labeled by the QSAR model, $c_1$ the number of inactive compounds correctly labeled by the QSAR model. Three parameters of performance were calculated: 1. accuracy on active compounds, $c_0/m_0$; 2. accuracy on inactive compounds, $c_1/m_1$; 3. overall accuracy on all of the compounds, $(c_0+c_1)(m_0+m_1)$. The derived binary QSAR model was cross-validated by a leave-one-out procedure.

In this procedure, only one object is eliminated at a time and the process is repeated until all objects have been eliminated once and only once. Accuracy was calculated for each step, and an average accuracy for all the steps was reported as a measure of the internal predictivity of the model within the training set.

A set of 410 compounds was chosen to be a training set to derive the binary QSAR model. The range of the biological activities (log RBA) was −2.02 to 2.60. Table 5 shows the data profiles with different threshold values.

A value of 1.7 of log RBA which corresponds to 50% of RBA was selected as the threshold to derive the binary QSAR model. Based on this threshold criterion, 62 compounds were active and 348 compounds were inactive in the training set. A smoothing factor was introduced to minimize the sensitivity of the derived model to the selection of bin boundaries as mentioned earlier. The binary QSAR model is also influenced by the number of principle components used. A 5×7 factor analysis was carried out to determine the effects of different smoothing factor values and principle component numbers on the binary QSAR analysis of the data set analyzed. Table 6 summarizes the results of the analysis.

In this study, two-dimensional (2D) molecular descriptors were used and were shown to perform well in compound clustering. In addition, Keir's shape indices were used, which contain implicit three-dimensional (3D) information. Explicit 3D descriptors were not considered to avoid bias of the analysis due to predicted conformational effects. The different combination of molecular descriptors have been systematically explored to identify a set that captures structural characteristics of estrogen analogs and resulting activities well. This was done for the learning set similar to more conventional QSAR analysis.

Table 6 shows that an optimal binary QSAR model was obtained by a combination of principal component numbers of 12 and a smoothing factor value of 0.12. Using this combination, the non-cross-validated accuracy is 85% on active compounds, 93% on inactive compounds, 92% for all the compounds. The cross-validated accuracy is 76% on active compounds, 93% on inactive compounds, and 90% for all the compounds. Any departure from these parameter values decreased the non-cross-validated and/or cross-validated accuracy. Thirteen molecular descriptors were used to derive the binary QSAR model (Table 7), including four atomic connectivity indices, four molecular shape indices, one total hydrophobic accessible surface area descriptor, one charge descriptor, one aromatic bond descriptor, and two indicator variables for specific functional group and molecular structure. One of the descriptor used is I,es. A number of desthylstilbestrol (DES) analogs are found to be more potent estrogen receptor ligands than estradiol itself, despite their structure similarity (log RBA is 2.48 for DES versus 2.00 for estradiol). Because structure features that account for higher potency of DES analogs were not obvious, the indicator variable I,es was included to account for this effect. A phenolic OH group that resembles the 3-OH of estradiol molecule is required for tight binding to estrogen receptor. To account for this specific structural effect, an indicator variable, I, OH, was used.

Figure 6:
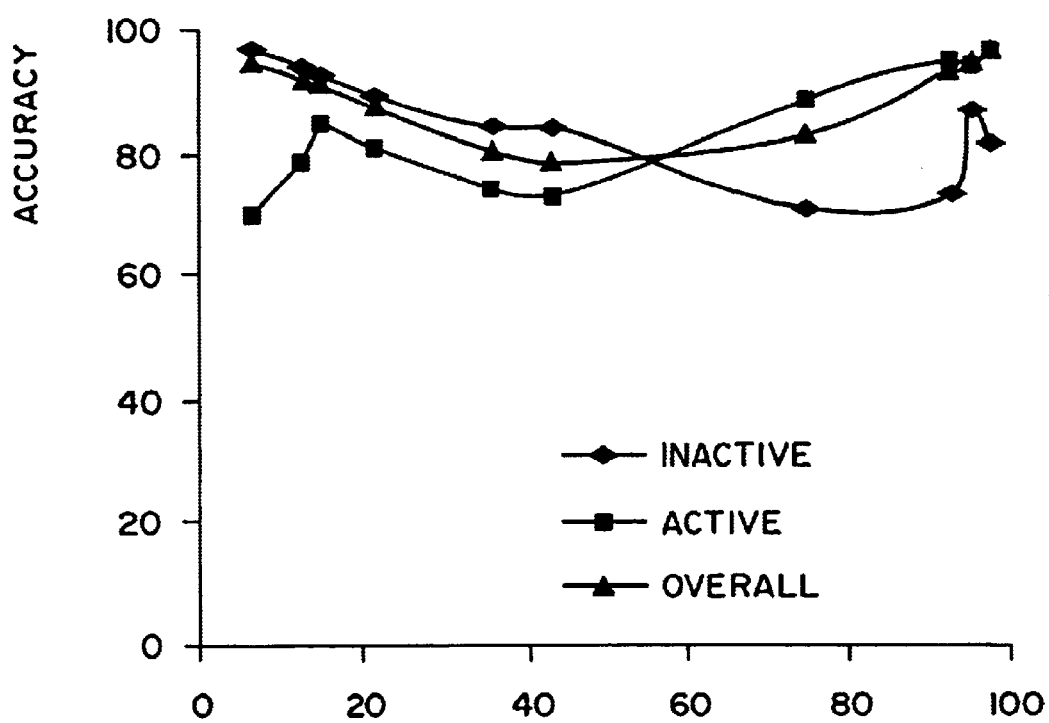
FIG. 6 is a graph of accuracy versus active percentage compounds.

The effects of ten different threshold values (log RBA values ranges from −2 to 2) on the binary QSAR model were analyzed (FIG. 2). Accuracy on active compounds ranged from 70% to 98%, with the highest accuracy obtained for 98% active compounds and the lowest for 7% active compounds. The overall accuracy remains stable at different threshold values (around 90%). FIG. 6 shows that selected threshold values cause fluctuation of observed overall accuracy by approximately 10%. The minimum obtained overall accuracy is about 80%. Thus, on the basis of these findings, the overall binary QSAR accuracy remains stable irrespective of the chosen threshold values.

Compounds with biological activity near the binary threshold value may fall into either the active or inactive category, which also depends on the experimental error. To analyze the influence of boundary effects on the binary QSAR model, compounds with log RBA values between 1.0 and 1.7 were omitted. Therefore, in these calculations, binary classification corresponds to largest difference in biological activities. This data set consisted of 292 inactive and 62 active (17.5%) compounds. In the resulting QSAR model, an accuracy 87% on active, 95% on inactive, and 93% for all 354 compounds was achieved. The performance is only slightly better than that obtained for the original training set. These results indicate that the boundary effects tested have only marginal influence on the binary QSAR accuracy, indicating that the binary QSAR model is stable. The obtained accuracy is not critically dependent on binary classification of observed activities, which is important with respect to the analysis of screening data.

In order to evaluate the predictive value of the binary QSAR model, 53 randomly selected estrogen analogs were tested. Seven out of 9 active compounds (78%), and 43 out 44 inactive compounds (98%) were correctly predicted (overall accuracy of 94%), which is consistent with the cross-validation result. The percentage of active compounds in the test set was 15%. If the compounds were selected and tested based on the binary QSAR model, the "hit rate" of active compounds would be 5 fold higher than randomly selected compounds even for this small data set.

The X-ray structures of the ligand binding domain of ER-α receptor in complex with estradiol and raloxifene have been reported in the past. The ligands are buried within the hydrophobic core of the ligand binding domain, but the polar ends of estradiol form hydrogen bonds to the only polar amino acid residues in the binding site. Glu353 forms a hydrogen bond to the A-ring phenolic hydroxyl group and His524 forms a hydrogen bond with 17β-hydroxyl group. The phenolic hydroxyl group is required for binding. The 3-OH group on estradiol can act as a hydrogen bond donor or acceptor, but the hydrogen bond donor ability is more important than the acceptor ability in stabilizing the complex. 3-Keto and 3-methyl ether derivatives have much lower binding affinities because they lack a hydrogen bond donor. The aromatic ring system is required for strong binding because analogs lacking aromatic moieties have only low binding affinity. It follows that structural differences between active and inactive compounds are distinct but may be quite limited. The estrogen analogs are considered to be a challenging test case for binary QSAR analysis because of small structural modifications, which actually change binary activity in a more continuous way, are considered here to render compounds either active or inactive.

Estrogen analogs have also been studied by conventional or classical QSAR techniques. Earlier QSAR studies on estrogen analogs did not reveal a consistent positive hydrophobic contribution for receptor-ligand binding, except substituents at the 11-β position of estradiol derivatives, although hydrophobicity expressed as log P(o/w) differs significantly among the analogs. Similarly, in the binary QSAR model, log P(o/w) was not found to be a significant descriptor. In contrast, ASA-H (which does not strictly correlate with log P(o/w) ($r^2$=0.62)) was found to be significant. This finding suggests that the strength of van der Waals/hydrophobic interactions between ligands and receptor is more important than the differences in energy required to desolvate the hydrophobic ligands.

Conventional QSAR based on regression techniques, such as multiple linear regression, partial least squares and, occasionally, neural networks, have been used to cluster compounds. These methods seek to minimize the squared error between the model and the observed data. This optimization of the model parameters introduces sensitivity to errors in experiments and regression analyses. In contrast, binary QSAR does not use any form of regression analysis; there is not attempt to minimize the model errors with regard to model parameters. It is a nonlinear modeling method. Because no regression is used, the model estimation procedure is very fast, which is in contrast to neural networks that require a lengthy training phase. Therefore, binary QSAR can efficiently process large data sets such as HTS data.

Several other clustering methods have been tested to classify compounds into different clusters. These methods are qualitative in that they are based on only chemical structural information regardless of biological activities. Compounds with similar structural features are clustered together. However, compounds with similar biological activities may appear in different clusters depending on their degree of structural similarity. In this case, identification of active clusters may be a nontrivial task. In contrast, binary QSAR takes both structure and activity information into account, and deduces a probability distribution function for novel compound to be either active or inactive.

While this invention has been described as having a preferred design, it is understood that it is capable of further modification, uses and/or adaptions following in general the principle of the invention and including such departures from the present disclosure as come within known or customary practice in the art to which the invention pertains, and as may be applied to the essential features set forth, and fall within the scope of the invention or the limits of the appended claims.

TABLE 1

| STRUCTURE | ACTIVITY |
| --- | --- |
| 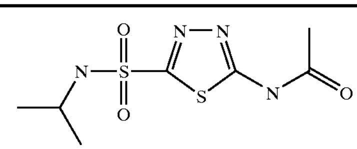 | 5.80 |
| 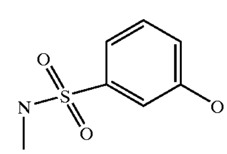 | 5.92 |
| . . . | . . . |
| 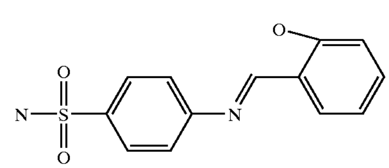 | 6.40 |

TABLE 2

| STRUCTURE | CLASS |
|---|---|
| [structure: isopropyl-sulfonamide-thiadiazole-acetamide] | 0 |
| [structure: N-methyl-benzenesulfonamide with hydroxyl] | 1 |
| [structure: sulfonamide-phenyl-imine-phenol] | 1 |
| ... | ... |

TABLE 3

| STRUCTURE (SMILES) | CLASS |
|---|---|
| CC(C)NS(O)(O)C1=NN—C(NC(C)=OS1 | 0 |
| CNS(O)(O)c1cccc([Cl])C1 | 1 |
| ... | ... |
| NS(O)(O)c1ccc(N=C—c2c(O)cccc1)cc1 | 1 |

TABLE 4

Composition of estrogen receptor ligands

| Category | representative structure | number of compounds |
|---|---|---|
| Estradiol derivatives | [estradiol structure] | 165 |
| 3-keto steroids | [3-keto steroid structure] | 2 |
| nonaromatic analogs | [nonaromatic steroid analog structure] | 4 |

TABLE 4-continued

Composition of estrogen receptor ligands

| Category | representative structure | number of compounds |
|---|---|---|
| metahexatrol derivatives | | 15 |
| hexestrol derivatives | | 50 |
| diethylstilbestrol derivatives | | 10 |
| tryphenylethylene analogs | | 40 |
| 2-phenylbezothiophene analogs | (OCH$_2$CH$_2$NC$_2$H$_{14}$) | 68 |
| 2-phenylindole analogs | | 61 |

TABLE 4-continued

Composition of estrogen receptor ligands

| Category | representative structure | number of compounds |
|---|---|---|
| indene analogs | 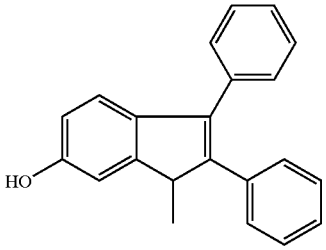 | 45 |
| Phenol and biphenols | 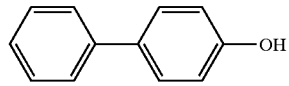 | 3 |

TABLE 5

Data Profiles at Different Binary Threshold Values

| threshold value (log RBA) | active compounds | inactive compounds | active % |
|---|---|---|---|
| −2.0 | 404 | 6 | 98% |
| −1.5 | 394 | 16 | 96% |
| −1.0 | 382 | 28 | 93% |
| 0.0 | 307 | 103 | 75% |
| 1.0 | 177 | 233 | 43% |
| 1.2 | 146 | 264 | 36% |
| 1.5 | 92 | 318 | 22% |
| 1.7 | 62 | 348 | 15% |
| 1.8 | 53 | 357 | 13% |
| 2.0 | 27 | 383 | 7% |

TABLE 6

Effects of PCA Number and Smoothing Factor on Binary QSAR

| PCA no. | smoothing factor | | | | | | |
|---|---|---|---|---|---|---|---|
|  | 0.08 | 0.10 | 0.12 | 0.14 | 0.16 | 0.20 | 0.25 |
| 6 | 0.79 | 0.76 | 0.74 | 0.69 | 0.69 | 0.60 | 0.52 |
|  | 0.63 | 0.61 | 0.60 | 0.60 | 0.55 | 0.48 | 0.45 |
| 8 | 0.81 | 0.77 | 0.77 | 0.76 | 0.76 | 0.73 | 0.66 |
|  | 0.71 | 0.71 | 0.71 | 0.69 | 0.68 | 0.65 | 0.55 |
| 10 | 0.85 | 0.84 | 0.84 | 0.84 | 0.81 | 0.77 | 0.73 |
|  | 0.68 | 0.68 | 0.66 | 0.68 | 0.69 | 0.68 | 0.65 |
| 12 | 0.85 | 0.85 | 0.85 | 0.82 | 0.81 | 0.81 | 0.79 |
|  | 0.69 | 0.71 | 0.76 | 0.76 | 0.73 | 0.73 | 0.71 |
| 13 | 0.85 | 0.85 | 0.82 | 0.82 | 0.82 | 0.82 | 0.79 |
|  | 0.63 | 0.66 | 0.69 | 0.69 | 0.69 | 0.66 | 0.68 |

TABLE 7

Molecular Descriptors Used in the Binary QSAR

| symbol | description |
|---|---|
| b-ar | number of aromatic bonds |
| ASA-H | total hydrophobic accessible surface area |
| $^0\chi$ | zero-order atomic connectivity index |
| $^0\chi^v$ | zero-order atomic valence connectivity index |
| $^1\chi$ | first-order atomic connectivity index |
| $^1\chi^v$ | first-order atomic valence connectivity index |
| $^1\kappa$ | Keir first shape index |
| $^2\kappa$ | Keir second shape index |
| $^3\kappa$ | Keir third shape index |
| $\Phi$ | Keir molecular flexibility index |
| Peoe-PC$^+$ | total of positive charge in Gasteiger & Marsili charge model |
| I,OH | indicator variable for phenolic hydroxy group; I,OH = 1 for compounds containing phenolic OH and 0 for other compounds |
| I,es | indicator variable for hexestrol derivatives; I,es = 1 for hexestrol compounds and 0 for other compounds. |

What is claimed is:

1. A method for developing a quantitative structure activity relationship for interaction between a particular biological target and at least one activity class of a training set of chemical compounds, comprising:

a) obtaining a training set of chemical compounds with molecular descriptors including a number of multidimensional vectors with an activity class for each of said vectors;

b) partitioning said multidimensional vectors into groups having interdependence;

c) transforming said descriptors such that said interdependence of said groups is lessened;

d) estimating a probability distribution of said descriptors by assuming that a probability distribution of a product of each of said groups is approximately equal to said probability distribution of said descriptors;

e) performing said partitioning, transforming and estimating steps for each of said activity classes;

f) developing a probability distribution for said activity classes; and g) using the probability distribution to develop a quantitative structure activity relationship for interaction between a particular biological target and at least one of said activity classes.

2. A method as recited in claim 1, wherein:

a) said training set of chemical compounds is obtained from high throughput screening data.

3. A method as recited in claim 1, wherein:
a) said training set of chemical compounds is comprised of virtual data.

4. A method as recited in claim 1, wherein:
a) said partitioning step is performed with computer software and computer hardware.

5. A method as recited in claim 1, wherein:
a) said transforming step is performed with computer software and computer hardware.

6. A method as recited in claim 1, wherein:
a) said developing step is performed with computer software and computer hardware.

7. A method as recited in claim 1, wherein:
a) said developing step is calculated with Bayes theorem.

8. A method as recited in claim 1, further comprising:
a) employing a smoothing factor with said estimated probability distribution of said descriptors from said estimating step.

9. A method as recited in claim 8, wherein:
a) said smoothing factor is a Gaussian distribution.

10. A method as recited in claim 1, further comprising:
a) cross-validating said quantitative structure activity relationship with said training set.

11. A method as recited in claim 1, wherein:
a) the particular target includes a ligand.

12. A method for predicting interaction activity of a candidate chemical compound and a particular biological target, comprising:
a) developing a prediction model comprising:
  i) obtaining a training set of chemical compounds with molecular descriptors including a number of multidimensional vectors with an activity class for each of said vectors;
  ii) partitioning said multidimensional vectors into groups having interdependence;
  iii) transforming said descriptors such that said interdependence of said groups is lessened;
  iv) estimating a probability distribution of said descriptors by assuming that a probability distribution of a product of each of said groups is approximately equal to said probability distribution of said descriptors;
  v) performing said partitioning, transforming and estimating steps for each of said activity classes;
  vi) developing a probability distribution for said activity classes;
b) obtaining a candidate chemical compound; and,
c) applying said prediction model to said candidate chemical compound to predict interaction activity of the candidate chemical compound and a particular biological target.

13. A method as recited in claim 12, wherein:
a) said developing a prediction model step is performed using a computer software program and computer hardware.

14. A method as recited in claim 12, wherein:
a) said candidate chemical compound is derived from experimental data.

15. A method as recited in claim 12, wherein:
a) said candidate chemical compound is derived from virtual data.

16. A method as recited in claim 12, wherein:
a) said applying step is performed by a computer software program and computer hardware.

17. A method as recited in claim 12, wherein:
a) said developing a prediction model step further includes employing a smoothing factor to said estimated probability distribution of said descriptors.

18. A method as recited in claim 17, wherein:
a) said smoothing factor is a Gaussian distribution.

19. A method as recited in claim 12, wherein:
a) said developing a prediction model further includes cross-validating a quantitative structure activity relationship with said training set.

20. A method as recited in claim 12, wherein:
a) the candidate chemical compound includes a ligand.

21. A method as recited in claim 13, wherein:
a) the candidate chemical compound includes a ligand.

22. A system for predicting interaction activity of candidate chemical compounds and a particular biolgical target as either active or inactive, comprising:
a) an analyzer being adapted to receive a training set of chemical compounds;
b) a prediction model being developed by said analyzer and based on said training set;
c) a sorter being adapted to receive a candidate chemical compound and said model from said analyzer, said sorter being adapted to apply said model to said candidate chemical compound to predict the interaction activity of the candidate chemical compound and the particular biological target;
d) said analyzer being adapted to receive the training set of chemical compounds, the training set of chemical compounds having molecular descriptors including a number of multidimensional vectors with an activity class for each of said vectors;
e) said analyzer being adapted to partition said multidimensional vectors into groups having interdependence;
f) said analyzer being adapted to estimate a probability distribution of said descriptors by assuming that a probability distribution of a product of each of said groups is approximately equal to said probability distribution of said descriptors;
g) said analyzer being adapted to develop a probability distribution for said activity classes; and
h) said analyzer being adapted to use the probability distribution to develop a quantitative structure activity relationship for interaction activity between a particular biological target and a candidate chemical compound as either active or inactive.

23. A system as recited in claim 22, wherein:
a) the candidate chemical compound includes a ligand.

24. A system as recited in claim 22, wherein:
a) said analyzer comprises a computer software program that is implemented with computer hardware.

25. A system as recited in claim 22, wherein:
a) said sorter comprises a computer software program that is implemented with computer hardware.

26. A system as recited in claim 22, further comprising:
a) a display device being coupled to said analyzer and said sorter, to display said model and said prediction of said activity of said candidate chemical compound.

27. A system as recited in claim 26, wherein:
a) said display device is a computer monitor.

28. A system as recited in claim 22, wherein:
a) said analyzer employs a smoothing factor with the estimating of a probability distribution of a product of each of the groups.

29. A system for predicting interaction activity of candidate chemical compounds and a particular biological target as either active or inactive, comprising:
  a) an analyzer being adapted to receive a training set of chemical compounds;
  b) a prediction model being developed by said analyzer and based on said training set;
  c) a sorter being adapted to receive a candidate chemical compound and said model from said analyzer, said sorter being adapted to apply said model to said candidate chemical compound to predict the interaction activity of said candidate chemical compound;
  d) said analyzer being adapted to receive said training set of chemical compounds, said chemical compounds having molecular descriptors including a number of multidimensional vectors with an activity class for each of said vectors;
  e) said analyzer being adapted to partition said multidimensional vectors into groups having interdependence;
  f) said analyzer being adapted to transform said descriptors such that said interdependence of said groups is lessened; and
  g) said analyzer being adapted to use the groups having transformed descriptors for predicting interaction activity of a candiate chemical compound and a particular biological target as being active or inactive.

30. A system as recited in claim 29, wherein:
  a) said analyzer comprises a computer software program that is implemented with computer hardware.

31. A system as recited in claim 29, wherein:
  a) said sorter comprises a computer software program that is implemented with computer hardware.

32. A system as recited in claim 29, further comprising:
  a) a display device being coupled to said analyzer and said sorter, to display said model and said prediction of said activity of said candidate chemical compound.

33. A system as recited in claim 32, wherein:
  a) said display device is a computer monitor.

34. A system as recited in claim 29, wherein:
  a) the candidate chemical compound includes a ligand.

35. A system for predicting interaction activity of candidate chemical compounds and a particular biological target as either active or inactive, comprising:
  a) an analyzer being adapted to receive a training set of chemical compounds;
  b) a prediction model being developed by said analyzer and based on said training set;
  c) a sorter being adapted to receive a candidate chemical compound and said model from said analyzer, said sorter being adapted to apply said model to said candidate chemical compound to predict the activity of said candidate chemical compound;
  d) said analyzer being adapted to receive said training set of chemical compounds, said chemical compounds having molecular descriptors including a number of multidimensional vectors with an activity class for each of said vectors;
  e) said analyzer being adapted to partition said multidimensional vectors into groups having interdependence;
  f) said analyzer being adapted to transform said descriptors such that said interdependence of said groups is lessened;
  g) said analyzer being adapted to estimate a probability distribution of said descriptors by assuming that a probability distribution of a product of each of said groups is approximately equal to said probability distribution of said descriptors;
  h) said analyzer being adapted to develop a probability distribution for said activity classes; and
  i) said analyzer being adapted to use the probability distribution to develop a quantitative structure activity relationship for interaction activity between a particular biological target and a candidate chemical compound as being active or inactive.

36. A system as recited in claim 35, wherein:
  a) said analyzer comprises a computer software program that is implemented with computer hardware.

37. A system as recited in claim 35, wherein:
  a) said sorter comprises a computer software program that is implemented with computer hardware.

38. A system as recited in claim 35, further comprising:
  a) a display device being coupled to said analyzer and said sorter, to display said model and said prediction of said interaction activity of said candidate chemical compound.

39. A system as recited in claim 38 wherein:
  a) said display device is a computer monitor.

40. A system as recited in claim 35, wherein:
  a) the candidate chemical compound includes a ligand.

* * * * *